United States Patent
Raney et al.

(10) Patent No.: US 7,476,202 B2
(45) Date of Patent: Jan. 13, 2009

(54) SAMPLING DEVICES AND METHODS UTILIZING A HORIZONTAL CAPILLARY TEST STRIP

(75) Inventors: Charles C. Raney, Camdenton, MO (US); Jeffrey N. Roe, San Ramon, CA (US); A. Michael Jung, Los Altos Hills, CA (US); Chris Wiegel, San Jose, CA (US); Steven N. Roe, San Mateo, CA (US); Edward P. Perez, Redwood City, CA (US); Rafael C. Donnay, Asbury, NJ (US); David S. Fisher, Stanford, CA (US); Ian M. Munson, Portland, OR (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 487 days.

(21) Appl. No.: 10/729,546

(22) Filed: Dec. 5, 2003

(65) Prior Publication Data

US 2004/0116829 A1 Jun. 17, 2004

Related U.S. Application Data

(63) Continuation of application No. PCT/US02/18278, filed on Jun. 7, 2002.

(60) Provisional application No. 60/296,949, filed on Jun. 8, 2001, provisional application No. 60/315,873, filed on Aug. 29, 2001.

(51) Int. Cl.
*A61B 5/00* (2006.01)
*B65D 81/00* (2006.01)

(52) U.S. Cl. .................................. 600/583; 600/573
(58) Field of Classification Search ................ 600/583, 600/573
See application file for complete search history.

(56) References Cited

U.S. PATENT DOCUMENTS 3,092,465 A 6/1963 Adams et al.

(Continued)

FOREIGN PATENT DOCUMENTS

JP 2000-199761 A1 7/2000

(Continued)

*Primary Examiner*—Max Hindenburg
*Assistant Examiner*—Jeffrey G Hoekstra
(74) *Attorney, Agent, or Firm*—Woodard, Emhardt, Moriarty, McNett & Henry LLP (57) ABSTRACT

Systems and methods for the sampling of bodily fluid from an incision in the skin include test strips which are positioned adjacent to the skin and which include features to inhibit the passage of the bodily fluid between the skin and the underside of the test strip. One system utilizes a sealing member located on the bottom surface of the test strip and positioned to provide a fluid tight seal with the skin. A second system includes a recessed surface aligned with the inlet opening of the test strip to preclude contact of the bodily fluid directly with the bottom surface of the test strip. A third system involves the use of a hydrophobic surface on the underside of the test strip to inhibit wicking of the bodily fluid along the test strip. The present invention further encompasses the combination of the foregoing sampling systems with each other, and with incising, expressing and/or testing systems and methods, particularly in a single, integrated device.

26 Claims, 6 Drawing Sheets

U.S. PATENT DOCUMENTS

| | | | |
|---|---|---|---|
| 3,298,789 A | 1/1967 | Mast | |
| 3,552,928 A | 1/1971 | Fetter | |
| 3,607,093 A | 9/1971 | Stone | |
| 3,630,957 A | 12/1971 | Rey et al. | |
| 3,802,842 A | 4/1974 | Lange et al. | |
| 3,964,871 A | 6/1976 | Hochstrasser | |
| 4,059,407 A | 11/1977 | Hochstrasser | |
| 4,061,468 A | 12/1977 | Lange et al. | |
| 4,477,575 A | 10/1984 | Vogel et al. | |
| 4,490,465 A | 12/1984 | Limbach et al. | |
| 4,774,192 A | 9/1988 | Terminiello et al. | |
| 4,924,879 A | 5/1990 | O'Brien | |
| 4,935,346 A | 6/1990 | Phillips et al. | |
| 4,994,238 A | 2/1991 | Daffern et al. | |
| 5,208,163 A | 5/1993 | Charlton et al. | |
| 5,306,623 A | 4/1994 | Kiser et al. | |
| 5,418,142 A | 5/1995 | Kiser et al. | |
| 5,451,350 A | 9/1995 | Macho et al. | |
| 5,456,835 A | 10/1995 | Castino et al. | |
| RE35,803 E | 5/1998 | Lange et al. | |
| 5,776,719 A | 7/1998 | Douglas et al. | |
| 5,824,491 A | 10/1998 | Priest et al. | |
| 5,857,983 A | 1/1999 | Douglas et al. | |
| 5,879,311 A | 3/1999 | Duchon et al. | |
| 5,951,492 A | 9/1999 | Douglas et al. | |
| 5,951,493 A | 9/1999 | Douglas et al. | |
| 5,962,215 A | 10/1999 | Douglas et al. | |
| 5,964,718 A | 10/1999 | Duchon et al. | |
| 6,015,392 A | 1/2000 | Douglas et al. | |
| 6,048,352 A | 4/2000 | Douglas et al. | |
| 6,066,103 A | 5/2000 | Duchon et al. | |
| 6,086,545 A | 7/2000 | Roe et al. | |
| 6,093,156 A * | 7/2000 | Cunningham et al. | 600/573 |
| 6,099,484 A | 8/2000 | Douglas et al. | |
| 6,132,449 A | 10/2000 | Lum et al. | |
| 6,183,489 B1 | 2/2001 | Douglas et al. | |
| 6,315,738 B1 * | 11/2001 | Nishikawa et al. | 600/583 |
| 6,332,871 B1 | 12/2001 | Douglas et al. | |
| 6,706,049 B2 | 3/2004 | Moerman | |
| 2002/0099308 A1 * | 7/2002 | Bojan et al. | 600/573 |
| 2002/0177761 A1 * | 11/2002 | Orloff et al. | 600/309 |

FOREIGN PATENT DOCUMENTS

| | | |
|---|---|---|
| WO | WO 98/24366 | 6/1998 |
| WO | WO 00/40150 | 7/2000 |
| WO | WO0040150 A1 | 7/2000 |

* cited by examiner

SAMPLING DEVICES AND METHODS UTILIZING A HORIZONTAL CAPILLARY TEST STRIP

This application is a continuation of PCT Application No. PCT/US02/18278, published in English and filed Jun. 7, 2002, which claims the benefit of U.S. Provisional Patent Application No. 60/296,949, filed Jun. 8, 2001 and U.S. Provisional Patent Application No. 60/315,873, filed Aug. 29, 2001, which are all incorporated herein by reference.

FIELD OF THE INVENTION

The present invention relates to the sampling of a bodily fluid obtained from an incision in the skin, and more particularly to acquiring the fluid with a test strip placed adjacent to the skin. The invention also may include the combination of such sampling devices and methods with incising, expressing, and/or testing systems.

BACKGROUND OF THE INVENTION

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

The testing of bodily fluids basically involves the steps of obtaining the fluid sample, transferring the sample to a test device, conducting a test on the fluid sample, and displaying the results. These steps are generally performed by a plurality of separate instruments or devices.

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re 35,803, issued to Lange, et al. on May 19, 1998; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties or constituents.

It has been known in the art to use test strips which are positioned adjacent to the skin in order to acquire a bodily fluid present at an incision site. Such uses are shown, for example, in U.S. Pat. No. 5,951,492, issued to Douglas et al. on Sep. 14, 1999; U.S. Pat. No. 6,099,484, issued to Douglas et al. on Aug. 8, 2000; and U.S. Pat. No. 6,332,871, issued to Douglas et al. on Dec. 25, 2001. The test strips are typically positioned against the skin or are held slightly above the skin, at a location which positions the fluid inlet of the test strip adjacent to the incision site. In these applications, however, it has been possible for the bodily fluid to move into the area between the underside of the test strip and the skin. The presence of a hydrophilic bottom surface of the test strip will tend to promote this movement of the fluid. Additionally, a narrow space between the test strip and the skin can function as a capillary passageway that draws the bodily fluid into the space. Any movement of the bodily fluid other than into the test strip inlet is undesirable since it reduces the chance of having a sufficient quantity of bodily fluid for analysis.

The present invention provides for enhancing the sampling of a bodily fluid received from an incision, particularly by promoting movement of the fluid into the test strip and by inhibiting movement of the fluid along the underside of the test strip.

SUMMARY OF THE INVENTION

The present invention provides various systems and methods for the sampling of bodily fluid from an incision in the skin. The sampling is achieved using a test strip which is positioned adjacent and parallel to the skin. The invention encompasses separate sampling devices as well as combination systems including incising, expression and/or testing systems.

In accordance with one aspect of the present invention, there is provided a test strip for acquiring a sample of a bodily fluid which includes a sealing member located on the bottom surface of the test strip and positioned to provide a fluid tight seal with the skin. In another aspect, the test strip includes a recessed surface aligned with the inlet opening of the test strip to preclude contact of the bodily fluid directly with the bottom surface of the test strip. A third aspect of the invention involves a test strip having a hydrophobic bottom surface to inhibit wicking of the bodily fluid along the test strip. The present invention further encompasses the combination of the foregoing systems with each other, and with incising, expressing and/or testing systems and methods, particularly in a single, integrated device.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and methods, and such further applications of the principles of the invention as illustrated therein being contemplated as would normally occur to one skilled in the art to which the invention relates.

The present invention provides a variety of devices and methods which separately or in combination are useful in enhancing the sampling of fluid from an incision in the skin. This sampling of the fluid utilizes structures to inhibit the movement of bodily fluid in the space between the test strip and the skin. The invention particularly relates to the use of a sealing member, recess and/or hydrophobic surfaces to block the bodily fluid, thereby directing the fluid to the inlet opening of the test strip.

The fluid is obtained from an incision formed in the surface of the skin. The incising of the skin may be accomplished by any suitable means, including cutting with a mechanical instrument, laser, high speed fluid stream, etc. Of these, lancing the skin is most common and is preferred, and specific descriptions herein use lancing for purposes of example. It will be appreciated, however, that lancing is only exemplary, and all forms of making an incision in the skin are included. As used herein, the term "incision" is intended to cover any opening in the skin that permits direct access to bodily fluid. The term "incising" is intended to mean generally any way to form an incision in the skin to enable fluid to be accessed directly. The term "incision site" is intended to include the site where an incision either has been or will be formed, unless from the context or express language it is clear otherwise.

The depth of penetration generally controls the fluid produced, particularly in combination with the characteristics of the incision site. The present invention is useful with various bodily fluids, including blood or interstitial fluid. The incising device may be configured for production of either blood or interstitial fluid, for example, by controlling the distance which the incising device extends into the user's skin. For example, a depth of 0.5 mm to 4 mm will typically produce blood from the dermis, while a depth of 0.1 mm to 0.5 mm will produce interstitial fluid from dermis or epidermis.

It will be appreciated from the following description that the present invention is useful independently of the presence or type of incising, expressing or testing systems. In certain embodiments, the present invention may comprise devices, and associated methods, which are limited only to sampling of fluid from an incision. In other embodiments, the sampling mechanisms and methods are combined with incising, expressing and/or testing systems. The present invention finds particular advantage in combination with such other systems as a part of an overall integrated device.

In one aspect of the present invention, there is provided a sealing member which is located on the underside of the test strip to inhibit the passage of bodily fluid along the bottom surface of the test strip. The sealing member is located to contact and seal with the skin adjacent to the incision. In certain embodiments, the test strip includes a sampling passageway opening along a perimetric edge of the test strip, in which case the sealing member preferably comprises a barrier extending across the test strip adjacent to the edge. In other embodiments, the test strip includes a sampling passageway opening into an interior aperture, in which case the sealing member preferably comprises a barrier surrounding the interior aperture.

A first preferred embodiment of the test strip system of the present invention is shown in FIGS. 1-4. The strip 10 is preferably combined in an integrated unit which further includes components for the purposes of incising the skin and testing the produced fluid sample. The test strip 10 includes a body 11 having first end 12, second end 13, top surface 14, and bottom surface 15. The body further includes an aperture 16 extending from the top surface to the bottom surface, a sampling passageway 17, and a test area 18. The sampling passageway 17 includes an inlet opening 19 which communicates with the aperture 16 at a location spaced from the bottom surface 15.

Figure 1:
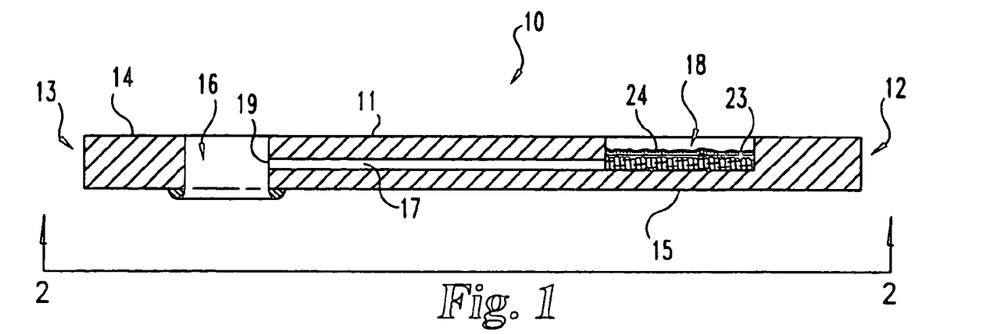
FIG. 1 is a side, cross-sectional view of a test strip in accordance with the present invention.

A sealing member 20 is attached to or formed integrally with the bottom surface 15 of the body 11 in a position surrounding the aperture 16. The sealing member is constructed from a biocompatible material such as silicon, urethane, rubber, latex and various other natural and synthetic materials. In one embodiment, the sealing member is configured and formed of a material to be deformable when pressed against the skin, helping to assure a fluid tight seal with the skin. Alternatively, the sealing member may be formed from a rigid material, such as a plastic, metal, ceramic or other material to provide a seal when pressed against the user's skin. In most instances a rigid material is equally useful because of the pliability of the skin. However, a deformable sealing member may be preferable in certain instances to further ensure that a fluid-tight seal forms with the skin.

In a further aspect, the sealing member preferably includes a hydrophobic surface. The seal with the skin will resist passage of the bodily fluid under the sealing member, but the use of a hydrophobic surface enhances the function of the sealing member. The surface of the sealing member may be provided to be hydrophobic in various known ways, all of which are intended to be encompassed by the present invention. For example, the sealing member may be formed from a hydrophobic material, or may be provided with a hydrophobic coating. In addition, certain hydrophilic materials can be treated to be made hydrophobic in accordance with known techniques.

Similarly, it is preferable for the test strip to include a hydrophobic bottom surface 15. The hydrophobic nature of the bottom surface may also be obtained in various ways as indicated in the preceding paragraph. In a preferred embodiment, the test strip of the present invention includes both a sealing member and a hydrophobic bottom surface, as shown for example in FIG. 1.

In an alternative embodiment (not shown), the test strip is configured without a sealing member, but includes a hydrophobic bottom surface. In such embodiments, the hydrophobic underside of the test strip operates to resist wicking of the bodily fluid between the test strip and the user's skin. It is not necessary that the entire bottom surface be hydrophobic, but rather that at least the portion of the bottom surface adjacent to the location of the incision be hydrophobic. In another aspect, the top surface is also made hydrophobic to resist the flow of bodily fluid along the top surface.

Figure 2:
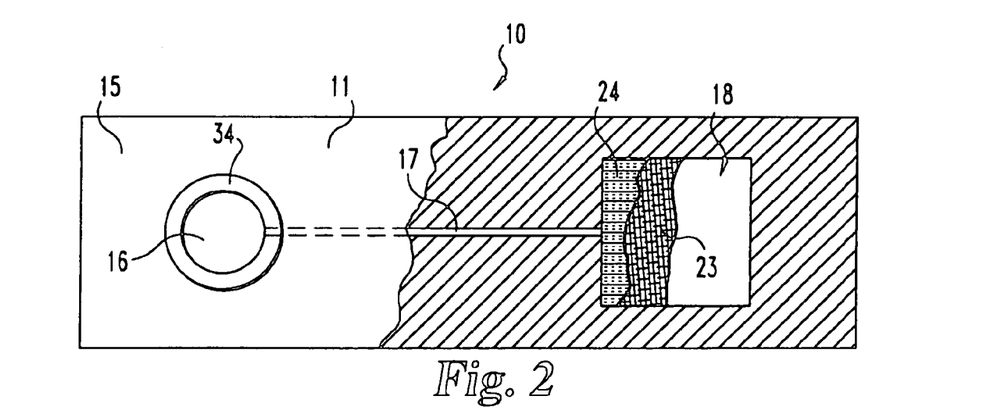
FIG. 2 is a bottom, plan view of the test strip of FIG. 1, partially in cross section.
Figure 3:
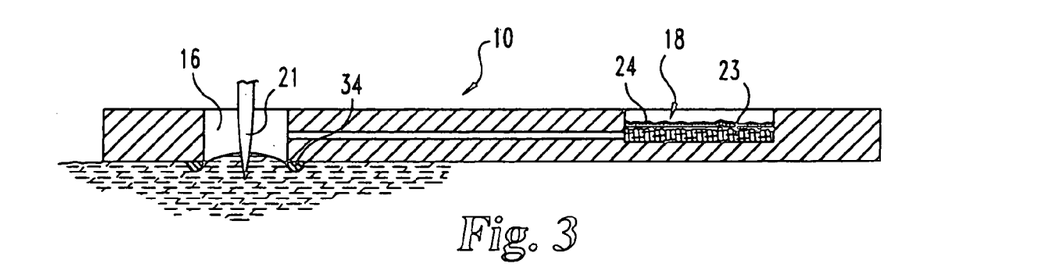
FIG. 3 is a side, cross-sectional view of the test strip of FIG. 1, showing the test strip positioned adjacent to the skin.

The use of the test strip system 10 proceeds as follows. The test strip 10 is positioned against the skin such that the skin bears against the sealing member 20, forming a fluid tight seal therewith. This assures that any fluid exiting the incision will be retained within the opening 16, rather than moving out under the test strip body. The sealing member further provides an expression force pulling on the skin to open the incision when formed. Also, the contact of the skin with the sealing member locates the skin at a controlled position to facilitate the formation of the incision at a desired depth and position. Because the sealing member projects outwardly from the bottom surface, the location of the skin within the opening is lowered, which in some embodiments is useful to position the skin at a desired location relative to the inlet opening 19 of the sampling passageway.

A lancing device 21 is extended downwardly through opening 16 to lance the skin to the desired, controlled depth. The lancet is then withdrawn (FIG. 4) and bodily fluid 21 is allowed to form at the incision site. When the fluid accumulates to a sufficient extent, it contacts the entrance 19 of the passageway 17 and is drawn into and through the passageway, such as by capillary action. The fluid moves to the test area 18, such as by wicking into an absorbent material 23, and there contacts the test reagent 24 positioned on top of the wicking material.

Figure 4:
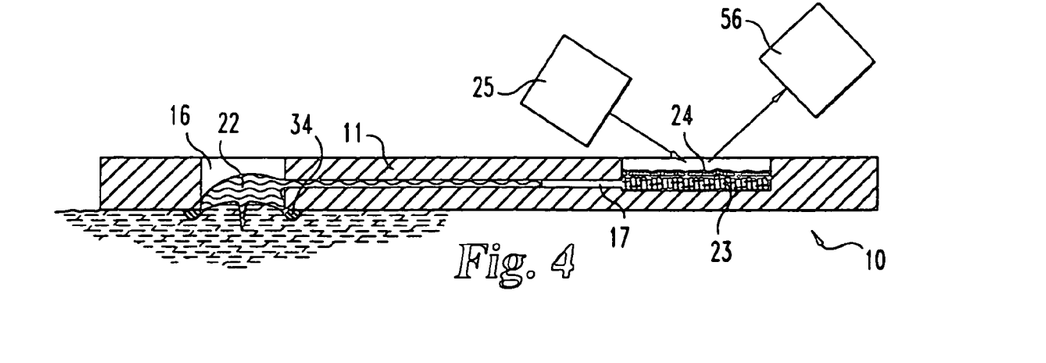
FIG. 4 is a side, cross-sectional view of the test strip of FIG. 1, showing the bodily fluid being acquired by the capillary passageway in the test strip.
Figure 5:
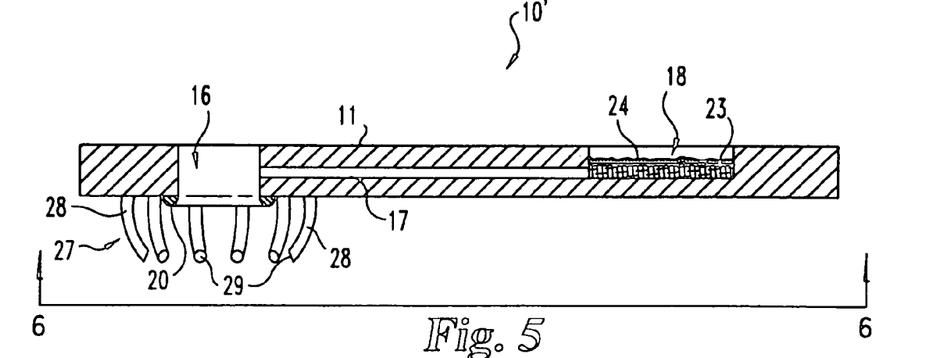
FIG. 5 is a side, elevational view of an integrated fluid testing device according to a second embodiment of the present invention which includes a fluid expression system.

The fluid is thereby presented in the test area and can be tested by conventional means, such as by reacting the fluid with the test reagent and analyzing the reaction product by optical or electrochemical means. For example, shown diagrammatically in FIG. 4 is a light source 25 for directing light against the test reagent, and a blood glucose meter 26 for receiving light reflected from the test reagent. In conventional fashion, the meter analyzes the reflected light to determine the result of the reaction between the bodily fluid and the test reagent. In this same manner, a wide variety of analytes and properties of the fluid may be determined. Useful optical, electrochemical and other test systems are well known in the art and therefore are not further described herein.

In an alternative embodiment, the test strip includes a constriction system utilizing several discrete members which engage the skin and pinch it inwardly to aid in expressing the bodily fluid from the incision. Referring in particular to FIGS. 5-8, there is shown an embodiment of the test strip 10' including a constricting system 27 attached to the underside thereof. The constricting system includes several discrete, deformable elements 28, each element defining a surface 29 to engage the skin and move it inwardly to constrict the skin.

Figure 6:
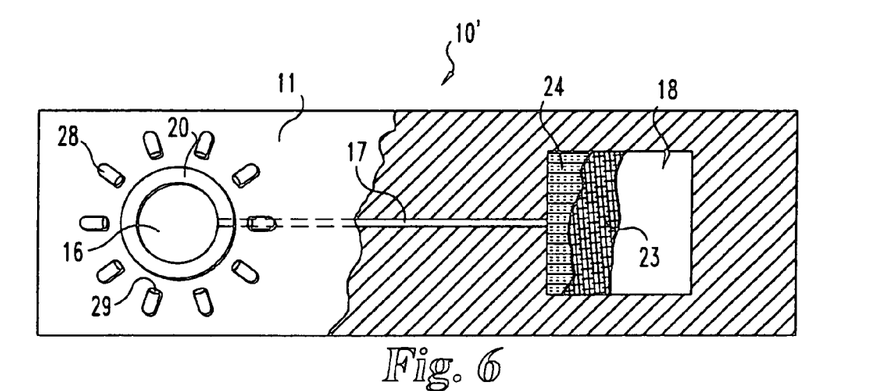
FIGS. 6-8 are partial, cross-sectional views of the fluid testing device of FIG. 5, showing in particular the acquisition of the fluid by the capillary passageway.
Figure 7:
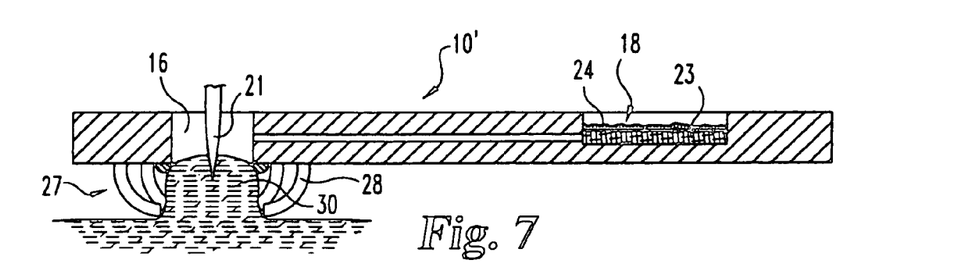
Figure 8:
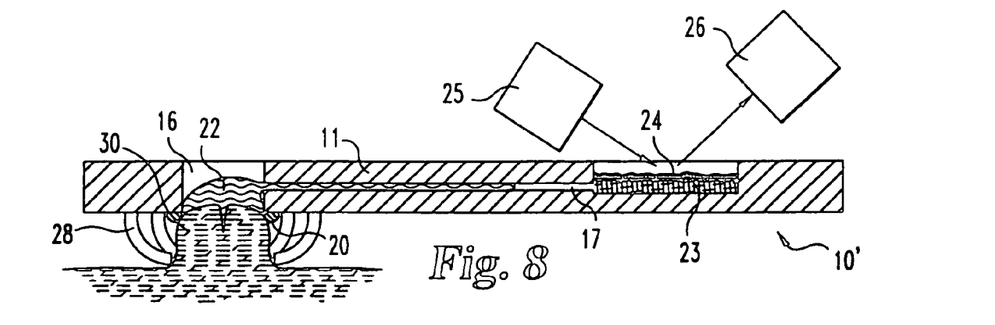

The constricting elements are selected to be spaced apart and to generally surround the incision site. The elements are therefore preferably provided such that at least two elements are positioned to be on opposite sides of the incision site, but also any additional number of elements may be included. In a preferred embodiment, the elements include skin-engaging surfaces 29 positioned to fall within a circular pattern (FIG. 6). The elements preferably deform in a manner to move the skin-engaging surfaces in a radially-inward direction.

The strip 10' otherwise is constructed substantially as shown in FIGS. 1-4, and is used as follows. The test strip 10' is pressed against the skin such that the arms 28 engage the skin and deform inwardly, thereby creating and retaining a bulged skin area 30. The skin is drawn upward and inward to an extent that it bears against the sealing member 16, forming a fluid tight seal therewith. This assures that any fluid exiting the incision will be retained within the opening 16, rather than moving out under the test strip body. The sealing ring further functions to pull on the skin, thus opening the incision when formed.

A lancing device 21 is extended downwardly through opening 16 to lance the skin to the desired, controlled depth. The lancet is then withdrawn (FIG. 8) and bodily fluid 22 is allowed to form at the incision site. When the fluid accumulates to a sufficient extent, it contacts the entrance of the passageway 17 and is drawn into and through the passageway to the test area 18.

In another aspect of the present invention, there is provided a test strip including a surface between the inlet opening and the bottom surface that is recessed away from the incision site. By recessing the bottom surface, the bodily fluid contacts the inlet opening before it contacts and is drawn along the bottom surface.

Referring to the drawings, there is shown a test strip 50 (FIG. 9) in accordance with another preferred embodiment of the present invention. Test strip 50 includes a body 51 having first end 52, second end 53, top surface 54 and bottom surface 55. The body further defines an aperture 56, a test area 57, and a sampling passageway 58 communicating with the aperture at an inlet opening 59 spaced from the bottom surface. The sampling passageway extends generally away from the aperture 56 in the direction of the first end 52.

Figure 9:
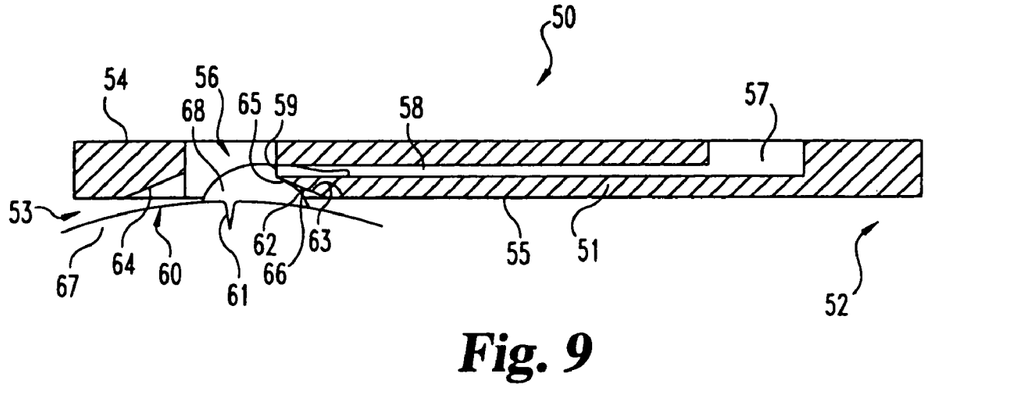
FIG. 9 is a side, cross-sectional view of an alternate embodiment of a test strip of the present invention.

The test strip is configured to promote contact of the bodily fluid with the inlet opening 59 prior to making contact with other portions of the test strip. An incision is made within the area encompassed by the aperture, and the desire then is to cause the bodily fluid coming from the incision to contact the inlet opening in preference to any of the surrounding portions of the test strip. In a preferred aspect of the present invention, this is accomplished by recessing at least a portion of the surface between the inlet opening and the bottom surface. In another aspect, the other portions of the bottom surface, for example the portion 60 on the opposite side of the aperture, are configured or located to inhibit contact with the bodily fluid. In one approach, the incision 61 is formed closer to the side of the aperture 56 at which the inlet opening is located. In another approach, the test strip may also include recessed portions at the other locations surrounding the incision site.

Accordingly, the test strip 50 includes a recessed surface 62 between the inlet opening 59 and the bottom surface 55. As used herein, the term "recessed surface" refers to the surface between the location of the inlet opening and the bottom surface. This surface is recessed in the direction away from the incision site, i.e., away from the aperture 56 in the direction of the first end 52. The term "recess" encompasses any configuration which displaces the closest portion of the planar, bottom surface 55 away from the aperture 56. For example, the surface could be curved inwardly or outwardly, or could have a series of steps of other contours.

As shown in FIG. 9, in a preferred embodiment the test strip includes a surface 62 which tapers away from the inlet opening 58 to the bottom surface 55. In this configuration, the surface 62 extends at an obtuse angle 63 from the bottom surface. In this embodiment, the surface 62 preferably extends from the bottom surface at an angle of from about 100 degrees to about 150 degrees, more preferably from about 120 to about 135 degrees.

Figure 10:
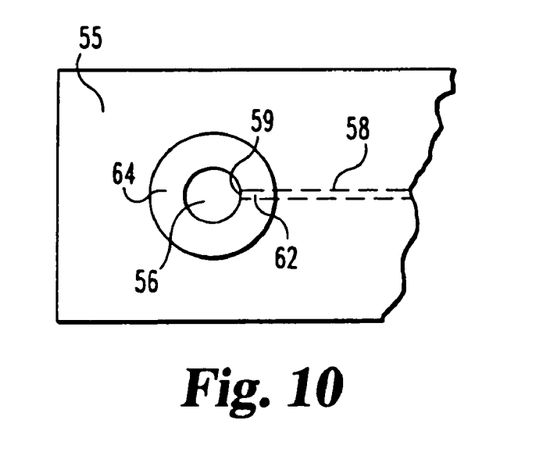
FIG. 10 is a partial, bottom plan view of the test strip of FIG. 9.

The test strip 50 may also include recessed portions at locations away from the inlet opening. For example, test strip 50 is shown including a recessed surface 64 on the side of the aperture opposite the inlet opening. Moreover, as shown more particularly in FIG. 10, the test strip may include a recessed surface which completely surrounds the aperture 56, thus providing a frusto-conical surface on the underside of the test strip.

The test strip 50 may also include a sealing member (not shown), as described with respect to FIGS. 1-4. Such a sealing member may be located along the recessed surface(s) and/or on the planar, bottom surface. The sealing member then complements the action of the recessed surfaces in that bodily fluid that happens to move against the sealing member will be inhibited from passing between the test strip and the skin.

The test strip may also be provided with a hydrophobic surface adjacent the aperture to further inhibit wicking away from the inlet opening. For example, the portions of the bottom surface adjacent to the aperture 56 are preferably provided with a hydrophobic surface. Further, the recessed surface 62 may be made hydrophobic to prevent wicking of the bodily fluid toward the bottom surface. In a particularly preferred embodiment, the recessed surface includes two different regions. A first region 65 adjacent the bottom surface is provided to be hydrophobic to inhibit wicking toward the bottom surface. A second region 66 adjacent the inlet opening is provided to be hydrophilic to promote wicking of the bodily fluid toward the inlet opening. Thus, fluid contacting the recessed surface will be directed away from the bottom surface and toward the inlet opening.

The test strip 50 is used as follows. The test strip is positioned adjacent to the skin, either resting against the skin or spaced slightly away from the skin. If a sealing member is included, then the test strip is placed sufficiently close to the skin to have the sealing member contact and seal with the skin. An incision 61 is formed in the skin 67, and a droplet 68 of bodily fluid forms at the incision site. As the droplet grows, it eventually contacts the inlet opening 59 and is drawn into the passageway 58, such as by capillary action. The recessing of surface 62 causes the droplet to contact the inlet opening in preference to contacting the bottom surface 55, thus avoiding the wicking of bodily fluid between the skin and the bottom surface. The droplet is precluded from wicking under the test strip in the areas away from the inlet opening by locating the incision relatively close to the inlet opening, and/or by the presence of additional recessed surfaces 64. The bodily fluid then moves through the passageway 58 to the test area 57 for analysis.

Figure 11:
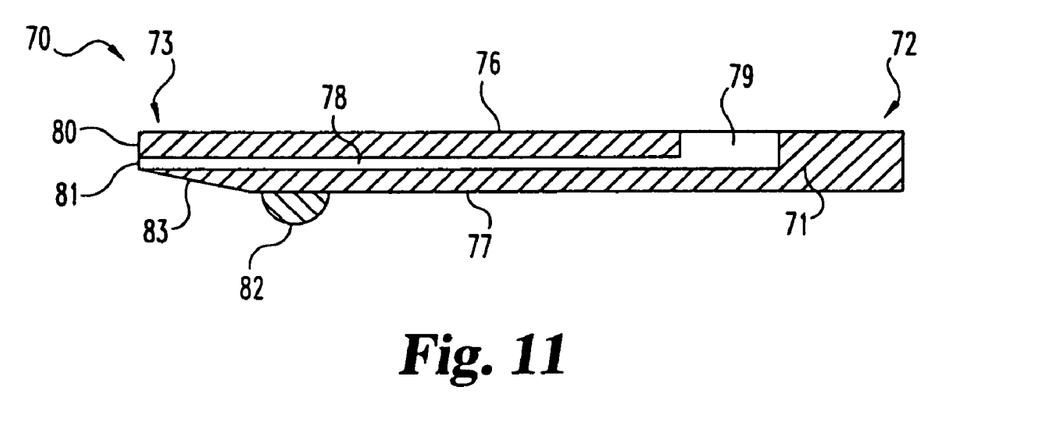
FIG. 11 is a side, cross-sectional view of another alternate embodiment of a test strip of the present invention.
Figure 12:
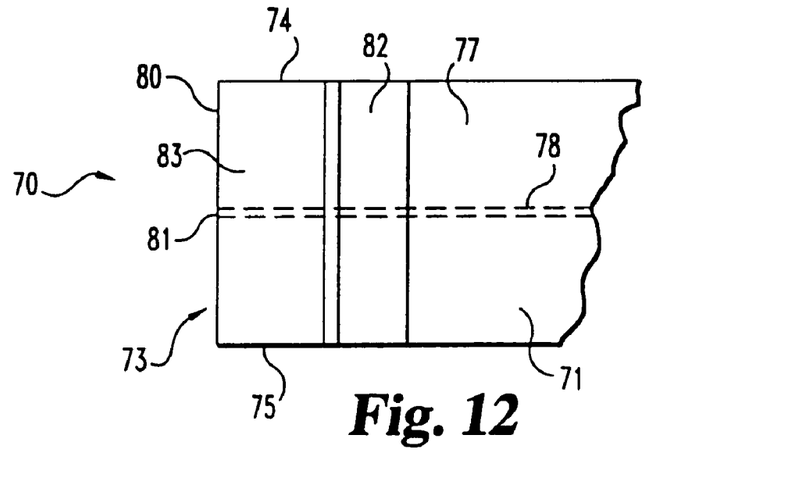
FIG. 12 is a partial, bottom plan view of the test strip of FIG. 11.

An alternate embodiment of the test strip of the present invention is shown in FIGS. 11 and 12. The test strip 70 includes a body 71 including a first end 72, second end 73, first side edge 74, second side edge 75, top surface 76 and bottom surface 77. The test strip 70 further defines a sampling passageway 78 communicating between a test region 79 and an end edge 80 located at the second end 73. The sampling passageway 78 includes an inlet opening 81 communicating with the end edge at a location displaced from the bottom surface 77.

A sealing member 82 is located on the bottom surface 77 in a position to contact and seal with the skin when the test strip is in use. The sealing member 82 is aligned under the inlet opening 81 such that bodily fluid present near the inlet opening is thereby blocked from passing under the test strip. In one embodiment, the sealing member preferably extends from the first edge 74 to the second edge 75. In an alternate embodiment (not shown), the sealing member extends less than the full width of the test strip, or is otherwise configured other than extending linearly across the test strip. For example, in one approach the sealing member forms a semi-circle contacting the end edge 80 at two locations on either side of the inlet opening. In another approach, the sealing member forms a V-shape extending inwardly of the test strip from the two corners formed between the end edge 80 and the two side edges 74 and 75.

The test strip 70 further includes additional features as described with respect to the previous embodiments. The test strip includes a recessed surface 83 connecting between the inlet opening 81 and the bottom surface 77. At least a lower portion of the recessed surface is preferably provided to be hydrophobic to preclude wicking of bodily fluid along the recessed surface toward the underside of the test strip. The sealing member 82 and the bottom surface 77 are also preferably provided to be hydrophobic to resist wicking of bodily fluid.

The test strip 70 is used in a similar fashion as the previous embodiments. The test strip is placed adjacent to the skin with the sealing member 82 pressing against and forming a seal with the skin. The sealing member may be rigid or deformable in order to provide a suitable seal. The test strip is positioned with the inlet opening 81 adjacent to the incision site. The incision is formed either before or after placement of the test strip. As the bodily fluid accumulates at the incision, it contacts the inlet opening and is drawn into the passageway 78. The features of the test strip 70, including the recessed surface 83, the sealing member 82, and the provision of hydrophobic surfaces individually and in combination inhibit the passage of the bodily fluid to the space between the test strip and the skin.

The following embodiments further demonstrate that the sampling systems are readily adapted for use with various incising, expressing and/or testing devices. Referring in particular to FIGS. 13-16, a typical lancing device is shown, except that it has been modified to include an exemplary sampling system in accordance with the present invention. The basic lancing device, absent the sampling system, is further described in U.S. Pat. No. Re 35,803, the disclosure of which is hereby incorporated by reference. Therefore, for illustrative purposes, only the major components of said device are shown in the drawings and described herein.

Figure 13:
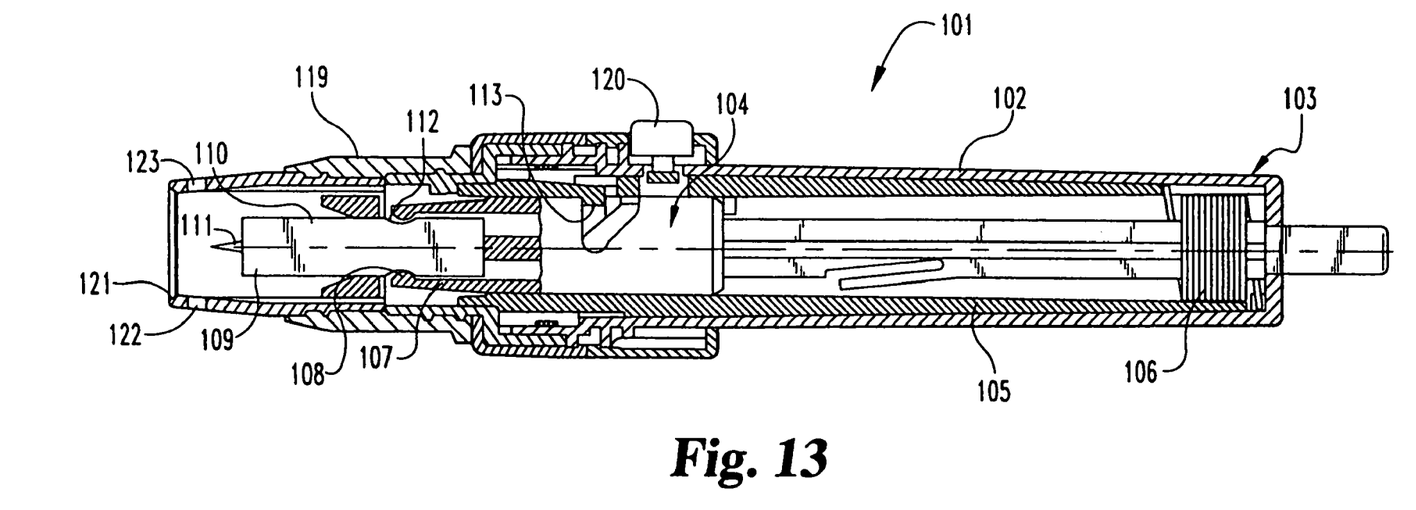
FIG. 13 is a side, cross-sectional view of a lancing device further incorporating a test strip system of the present invention.
Figure 14:
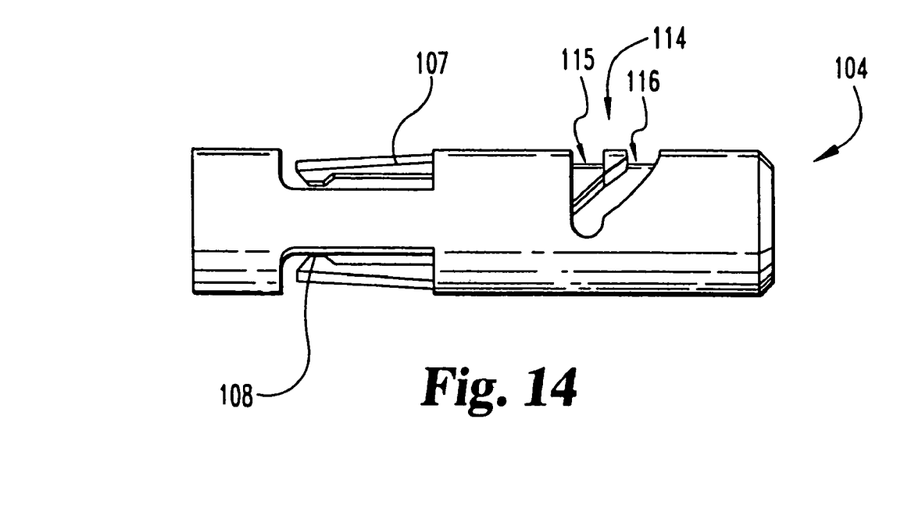
FIG. 14 is a side, elevational view of a lancet holder useful in the device of FIG. 13.

The lancing device 101 includes a housing 102 which contains a lancet drive mechanism 103 and a lancet holder 104. The drive mechanism includes a rotatable sleeve 105 and a spirally-wound, coiled spring 106 coupled between the housing and the rotatable sleeve. The lancet holder 104 is longitudinally slidable within the sleeve 205 and includes arms 107 with end lugs 108 that are receivable within recesses formed in a lancet component. The lancet component 109 includes a body 110 and a lancet tip 111. The lancet body defines a circumferential recess 112 which receives the end lugs 108 of the arms of the lancet holder 104. The lancet 109 is thereby longitudinally movable inside of the sleeve 105 in concert with the movement of the lancet holder 104.

The rotatable sleeve 105 includes a drive pin 113, and the lancet holder 104 defines a driver cam 114. The driver cam includes a first cam segment 115 to allow for cocking of the mechanism. The driver cam further includes a second, symmetrical, arcuate cam segment 116 to provide for projection and withdrawal of the lancet tip relative to the housing opening 117 formed in the pressing member 118 of the housing. An outer ring 119 connects with the rotatable sleeve 105 and upon rotation of the outer ring the sleeve is also rotated to tension the spring 106 as the drive pin 113 moves within the first cam segment 115. The rotatable sleeve automatically locks once in the fully tensioned position.

Upon pressing a lock release button 120, the sleeve rotates back to its original position. During this return rotation, the drive pin 113 moves within the second cam segment 116, causing the lancet holder and lancet initially to translate longitudinally of the sleeve 105 and housing 102 in a direction to drive the lancet tip to incise the skin. The lancet tip 111 is immediately thereafter withdrawn by operation of the second cam segment 116 of the lancet holder.

Figure 15:
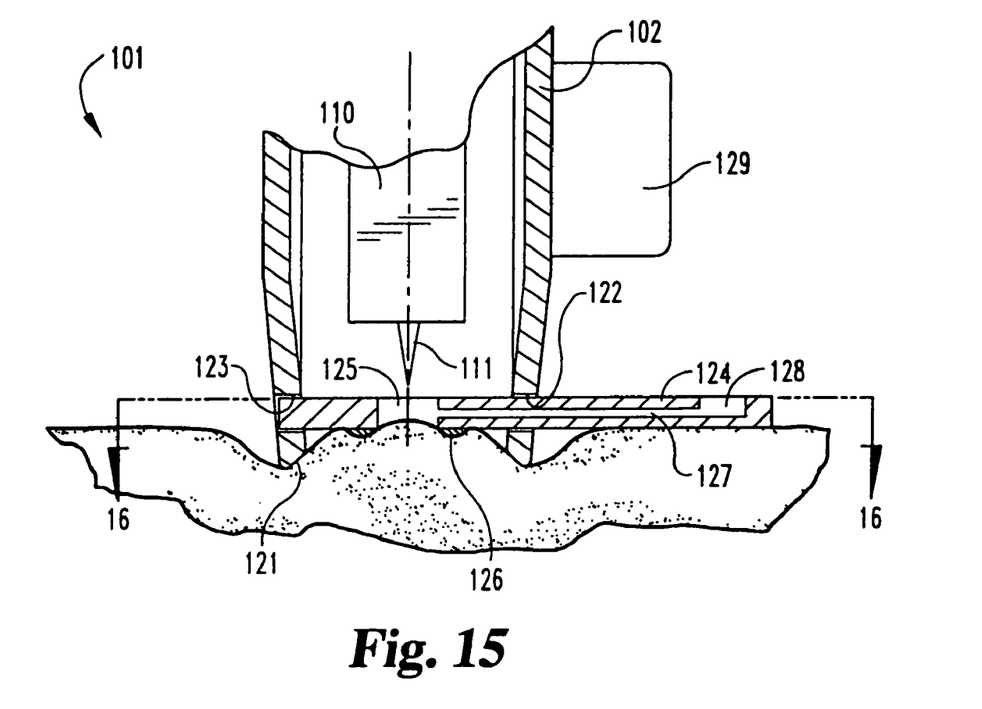
FIG. 15 is a partial, cross-sectional view of the skin-engaging portion of the device of FIG. 13, and further showing the test strip mounted therein.
Figure 16:
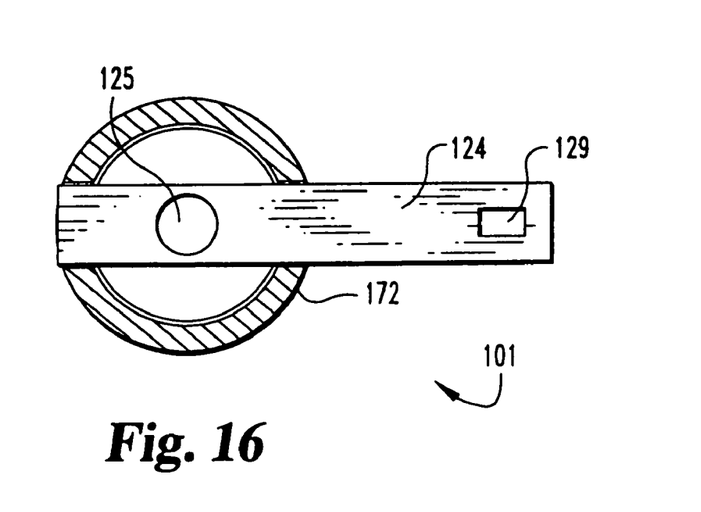
FIG. 16 is a cross-sectional view of the device of FIG. 13 taken along the line 13-13 and viewed in the direction of the arrows.

The pressing member extends to an annular surface 121 and defines slots 122 and 123 adjacent thereto. A test strip 124 (FIG. 15) is received within the slots 122-223 and includes an aperture 125 which is thereby positioned in line with the lancet 111. The test strip includes a sealing member 126 forming a ring surrounding the aperture 125, and further includes a capillary passageway 127 that extends from an inlet opening which communicates with the aperture 125 to a test region 128. The test region includes suitable reagent to interact with the bodily fluid which is received in the test region. An optical test device 129 is mounted to the housing and is positioned to evaluate the results of the reaction in the test region.

In accordance with the present invention, the integrated device 101 is operable as follows. The device is pressed against the skin 130, which thereby bears against the annular surface 121 and the sealing member 126. The lancet 111 is then advanced through the aperture 125 in the test strip and incises the skin. As a fluid droplet forms, it contacts the inlet opening of the capillary passageway 127 and is transported to the test region 128. The fluid then reacts with the reagent provided in the test region, and the results are read by the test device 129. The test strip may additionally include a recessed surface, as previously described, to further inhibit the passage of fluid between the skin and the underside of the test strip.

The foregoing description provides a representative sample of a lancing device useful in combination with the test strips of the present invention. It will be appreciated, however, that the particular lancing device and method are not limiting to the present invention, which finds utility with innumerable lancing systems. By way of further example, other representative lancing mechanisms include those shown in U.S. Pat. Nos. 4,924,879, issued to O'Brien on May 15, 1990; U.S. Pat. No. 5,879,311, issued to Duchon et al. on Mar. 9, 1999; U.S. Pat. No. 5,857,983, issued to Douglas et al. on Jan. 12, 1999; U.S. Pat. No. 6,015,392, issued to Douglas et al. on Jan. 18, 2000; U.S. Pat. No. 6,048,352, issued to Douglas et al. on Apr. 11, 2000; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 6,332,871, issued to Douglas et al. on Dec. 25, 2001; U.S. Pat. No. 5,964,718, issued to Duchon et al. on Oct. 12, 1999; U.S. Pat. No. 6,066,103, issued to Duchon et al. on May 23, 2000; and U.S. Pat. No. 6,086,545, issued to Roe et al. on Jul. 11, 2000.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A sampling system, comprising:
a test strip configured for loading into a lancing device to analyze body fluid from an incision created by the lancing device, wherein the test strip has a strip shape, wherein the test strip has a first end and a second end opposite the first end, the test strip includes an end edge at the second end, the test strip including
a test area configured to analyze the body fluid,
a sampling passageway with an inlet opening that is remotely located from the test area, the inlet opening being defined in the end edge at the second end, the sampling passageway being sized and configured to draw the body fluid via capillary action, the sampling passageway extending from the inlet opening to the test area for transporting the body fluid from the incision to the test area via capillary action,
a bottom surface that faces a skin when the test strip is received in the lancing device, and
a sealing member projecting outwardly from the bottom surface of the test strip proximal the inlet opening and positioned to seal with the skin when the test strip is pressed against the skin to retain the body fluid at the inlet opening, wherein the sealing member is located on the bottom surface between the first end and the end edge at the second end, wherein the sealing member is made of a deformable material that deforms upon pressing against the skin, wherein the sealing member extends along the bottom surface at a location where the sealing member is sandwiched between the bottom surface of the test strip and the skin when the test strip is pressed against the skin, wherein the sealing member is configured to inhibit flow of the body fluid between the bottom surface of the test strip and the skin;
wherein the test strip with the sealing member is configured to be unloaded from the lancing device as a single disposable unit; and
wherein the sealing member has a surface that is hydrophobic.

2. The test strip of claim 1, wherein the test strip has a recessed surface extending between the inlet opening and the bottom surface.

3. The system of claim 1, further comprising:
the lancing device including a housing and a lancet driver with a lancet disposed in the housing for lancing the incision in skin, the housing including a skin contacting surface where the lancing device contacts the skin during lancing.

4. The system of claim 3, wherein:
the test strip defines an aperture;
the lancet is positioned to extend through the aperture in the test strip during lancing;
the inlet opening communicates with the aperture; and
the sealing member surrounds the aperture on the bottom surface of the test strip.

5. The system of claim 4, wherein:
the test strip has a recessed surface extending between the inlet opening and the bottom surface; and
the recessed surface has a frustoconical shape.

6. The system of claim 1, wherein:
the test strip includes a top surface positioned opposite the bottom surface; and
the test area includes an opening that is open at the top surface of the test strip to permit reflectance of light for optical analysis.

7. The system of claim 1, wherein:
the test strip includes a top surface positioned opposite the bottom surface; and
at least a portion of the top surface is hydrophobic to resist flow of the body fluid along the top surface.

8. The system of claim 1, wherein at least a portion of the bottom surface is hydrophobic.

9. The test strip of claim 2, wherein the recessed surface extends at an obtuse angle from the bottom surface to the inlet opening.

10. The test strip of claim 9, wherein the obtuse angle is from about 100 degrees to about 150 degrees.

11. The test strip of claim 1, wherein:
the test strip has an end edge; and
the inlet opening communicates with the end edge at a location spaced from the bottom surface.

12. The test strip of claim 11, wherein the test strip further includes first and second side edges extending from the end edge, the sealing member extending from the first side edge to the second side edge.

13. The system of claim 1, wherein the sealing member extends in a linear manner across the bottom surface.

14. The system of claim 1, wherein the inlet opening is hydrophilic.

15. The system of claim 1, wherein the recessed surface is hydrophobic and the inlet opening is hydrophilic.

16. A sampling system, comprising:
a test strip configured for loading into a lancing device to analyze body fluid from an incision created by the lancing device, wherein the test strip has strip shape, wherein the test strip has a first end and a second end opposite the first end, the test strip includes an end edge at the second end, the test strip including
a test area configured to analyze the body fluid,
a sampling passageway with an inlet opening that is remotely located from the test area, the inlet opening being defined in the end edge at the second end, the sampling passageway being sized and configured to draw the body fluid via capillary action, the sampling passageway extending from the inlet opening to the test area for transporting the body fluid from the incision to the test area via capillary action,
a bottom surface that faces a skin when the test strip is received in the lancing device,
a sealing member projecting outwardly from the bottom surface of the test strip, wherein the sealing member is made of a deformable material that deforms upon pressing against the skin, and
the test strip having a recessed surface extending between the inlet opening and the bottom surface to inhibit contact of the body fluid on the skin with the bottom surface of the test strip, wherein the recessed surface tapers away from the inlet opening at the end edge to the bottom surface, wherein the recessed surface extends from the end edge at the second end to the sealing member, wherein the recessed surface at the end edge with the inlet opening is located farther away from the skin than the recessed surface at the bottom surface during drawing of the body fluid from the incision; and wherein the test strip with the recessed surface is configured to be unloaded from the lancing device as a single disposable unit.

17. The system of claim 16, further comprising:

the lancing device including a housing and a lancet driver with a lancet disposed in the housing for lancing the incision in skin, the housing including a skin contacting surface where the lancing device contacts the skin during lancing.

18. The system of claim 16, wherein:

the test strip includes a top surface positioned opposite the bottom surface; and the test area includes an opening that is open at the top surface of the test strip.

19. The system of claim 16, wherein:

the test strip includes a top surface positioned opposite the bottom surface; and at least a portion of the top surface is hydrophobic to resist flow of the body fluid along the top surface.

20. The system of claim 16, wherein at least a portion of the bottom surface is hydrophobic.

21. The system of claim 20, wherein the recessed surface is hydrophobic.

22. The test strip of claim 21, wherein the obtuse angle is from about 100 degrees to about 150 degrees.

23. The test strip of claim 16, wherein the recessed surface extends at an obtuse angle from the bottom surface to the inlet opening.

24. The system of claim 16, wherein the recessed surface is hydrophobic and the inlet opening is hydrophilic.

25. The system of claim 16, wherein the test strip at the inlet opening is thinner than at the bottom surface.

26. The system of claim 16, wherein the sealing member extends in a linear manner across the bottom surface.

* * * * *